United States Patent
Rutter et al.

(10) Patent No.: US 10,335,484 B2
(45) Date of Patent: Jul. 2, 2019

(54) METHODS OF GENERATING ROBUST PASSIVE AND ACTIVE IMMUNE RESPONSES

(71) Applicant: HUMABS BIOMED SA, Bellinzona (CH)

(72) Inventors: William Rutter, San Francisco, CA (US); Davide Corti, Bellinzona (CH)

(73) Assignee: HUMABS BIOMED SA, Bellinzona (CH)

( * ) Notice: Subject to any disclaimer, the term of this patent is extended or adjusted under 35 U.S.C. 154(b) by 0 days.

(21) Appl. No.: 14/759,381

(22) PCT Filed: Jan. 8, 2014

(86) PCT No.: PCT/US2014/010621
§ 371 (c)(1),
(2) Date: Jul. 6, 2015

(87) PCT Pub. No.: WO2014/110092
PCT Pub. Date: Jul. 17, 2014

(65) Prior Publication Data
US 2016/0008461 A1    Jan. 14, 2016

Related U.S. Application Data (60) Provisional application No. 61/750,340, filed on Jan. 8, 2013.

(51) Int. Cl.
| | |
|---|---|
| A61K 39/395 | (2006.01) |
| A61K 39/42 | (2006.01) |
| A61K 39/00 | (2006.01) |
| C07K 16/10 | (2006.01) |
| A61K 39/12 | (2006.01) |

(52) U.S. Cl.
CPC ............ *A61K 39/395* (2013.01); *A61K 39/00* (2013.01); *A61K 39/12* (2013.01); *A61K 39/42* (2013.01); *C07K 16/10* (2013.01); *C07K 16/1018* (2013.01); *A61K 2039/505* (2013.01); *A61K 2039/507* (2013.01); *A61K 2039/545* (2013.01); *C07K 2317/76* (2013.01); *C12N 2760/16134* (2013.01); *C12N 2760/20134* (2013.01)

(58) Field of Classification Search
None
See application file for complete search history.

(56) References Cited

U.S. PATENT DOCUMENTS

| | | |
|---|---|---|
| 5,972,347 A | 10/1999 | Eder et al. |
| 6,136,319 A | 10/2000 | Whitfill et al. |
| 2003/0044414 A1 | 3/2003 | Thoma et al. |

FOREIGN PATENT DOCUMENTS

| | | |
|---|---|---|
| WO | 2004014314 A2 | 2/2014 |

OTHER PUBLICATIONS

Lelie et al., Hepatology, 1986, 6(5):971-975.*
Kroger et al., MMWR, Recommendations and Reports, Dec. 1, 2006, 55(RR15):1-48, available from www.cdc.gov/mmwr/preview/mmwrhtml/rr5515a1.htm, website accessed on Jul. 11, 2017, printout version 72 pages.*
Theppisai et al., Int. J. Gynecol. Obstet., 1990, 32:353-357. (Year: 1990).*
Assad and Francis, Vaccine, 2000, 18:57-67. (Year: 2000).*
Lee et al., BMJ, 2006, 332(7537):328-336. (Year: 2006).*
Shin et al., Antiviral Research, 2007, 75:113-120. (Year: 2007).*
International Search Report and Written Opinion, PCT Application No. PCT/US2014/060621, dated Apr. 30, 2014, 12 pgs.

* cited by examiner

*Primary Examiner* — Stacy B Chen
(74) *Attorney, Agent, or Firm* — Seed IP Law Group LLP (57) ABSTRACT

The invention relates to methods of generating a robust passive and an active immune response in a subject comprising administering a neutralizing antibody and a pathogen to the subject. The invention also relates to kits and pharmaceutical compositions useful in generating a robust passive and an active immune response in a subject.

13 Claims, 3 Drawing Sheets

METHODS OF GENERATING ROBUST PASSIVE AND ACTIVE IMMUNE RESPONSES

This application claims the benefit of priority of U.S. provisional Application No. 61/750,340, filed Jan. 8, 2013, the disclosure of which is hereby incorporated by reference, as if written herein, in its entirety.

BACKGROUND

Field of the Invention

The present invention relates to the field of immunology. More particularly, the present invention relates to improved methods for inducing immune responses due to infection by pathogenic agents by combining passive and active immunization, and to antibodies that enhance a subject's endogenous immunological response to a pathogen or to cancer cells.

Description of Related Art

Immunity encompasses the ability of the human body to both tolerate the presence of endogenous ("self") material, and to eliminate foreign ("non-self") material, such as infectious agents including viruses, bacteria, fungi, protozoa, etc., and can be achieved via two basic mechanisms: active immunity and passive immunity.

Active immunity is protection provided by one's own immune system, and involves stimulation of the immune system to produce antigen-specific humoral (antibody) and cellular immunity. Unlike temporary passive immunity, active immunity is more permanent, lasting for many years, or for a lifetime. The persistence of such long-lasting protection is known as "immunological memory." Following exposure of the immune system to an antigen, memory B-cells continue to circulate in the blood and reside in the bone marrow for many years. Upon reexposure to the antigen, memory B-cells begin to replicate and rapidly produce antibody, reestablishing protection. Active immunity can be acquired in either of two ways: either by having the natural disease, or by vaccination. Vaccines generate an immune response and prevent the infection with the corresponding infectious pathogen.

Passive immunity is provided by introducing products into the body, such as antibodies, produced by an animal or a human. This is usually achieved by injection. Passive immunity provides effective short-lived protection that disappears within a few weeks or months due to catabolism of the immunity-conferring product.

The immune system identifies foreign ("non-self") substances, referred to as antigens. Antigens can be either live organisms, inactivated/attenuated organisms, or immune system-stimulating peptides, proteins, cell wall polysaccharides, etc., derived from host pathogens. The most effective antigens are generally live organisms. In response to an antigen, the immune system develops defensive antibodies (or immunoglobulins) and specific T cells (cell-mediated immunity) that facilitate elimination of foreign substances, referred to as the "immune response."

There are several basic types of vaccines:
Live, unattenuated vaccines comprising a disease-causing pathogen;
Live, attenuated vaccines comprising a modified disease-causing pathogen that retains the ability to replicate and produce immunity, but which does not cause illness. Examples include vaccines containing live viruses and bacteria. Active immunity from a live attenuated vaccine may not develop due to interference from circulating antibody to the pathogen. Furthermore, antibody from any source can interfere with the growth of the vaccine pathogen, leading to a poor response, or no response, to the vaccine.

Inactivated vaccines comprising whole disease-causing pathogens that cannot replicate, or various fractions of such pathogens. The latter can be either protein-based or polysaccharide-based.

Recombinant vaccines in which structural elements of the infectious pathogen are produced by recombinant DNA methods, in essence mimic all, or a portion, of the pathogen. Such vaccines are produced biologically, and when accompanied with an appropriate adjuvant, can produce a potent and neutralizing response. Examples of such vaccines include the Hepatitis B vaccine, the meningococcus B vaccine, etc. However, attempts to produce "subunit vaccines", comprised of components (e.g., peptides) of viruses have been largely unsuccessful. Such examples include HSV, HIV, etc. Further, attempts to produce vaccines from DNA or RNA from the viruses have also met with little success.

In view of the foregoing, there is a need for improved methods and agents capable of generating an immunologically protective response in subjects infected by, or at risk for infection by, a pathogen.

SUMMARY

The invention is based, in part, on the discovery of potent antibodies which neutralize most, if not all, genetic variants of viruses and a method of generating a passive and an active immune response in a subject by the administration of a neutralizing antibody with a pathogen. Accordingly, in one aspect of the invention, the invention comprises methods for generating, stimulating or eliciting an active vaccine or immune response in a subject, or ameliorating or eliminating the severity of an infection in a subject, or limiting infection of a subject by a pathogen.

In one embodiment of the invention, the invention comprises a method of generating an active vaccine response in a subject comprising administering a neutralizing antibody concurrently or sequentially with an antigen. The antigen could, for example, be an active wild type; unattenuated; attenuated; partially inactivated; or totally inactivated infectious pathogen. In another embodiment, the invention comprises a method of stimulating an active immune response in a subject, comprising administering to the subject an effective amount of an antibody and an antigen, wherein the antigen is an infectious pathogen that causes disease or is equivalent to a pathogen that causes a disease, and wherein the antibody neutralizes infectivity of the pathogen. In yet another embodiment, the invention comprises a method of ameliorating or eliminating the severity of an infection, comprising administering to a subject in need thereof an effective amount of an antibody and an antigen, wherein the infection is caused by the antigen, wherein the antigen is an infectious pathogen that causes a disease or is equivalent to a pathogen that causes a disease, and wherein the antibody neutralizes infectivity of the pathogen. In yet another embodiment, the invention comprises a method of limiting infection of a subject by a pathogen, comprising administering to a subject in need of such protection an effective amount of an antibody and an antigen, wherein the antigen is an infectious pathogen that causes a disease or an equivalent thereof; and wherein the antibody neutralizes infectivity of the pathogen.

In another aspect, the invention comprises a method of ameliorating or eliminating the severity of an existing infection caused by a pathogen, comprising administering to a subject in need thereof an effective amount of an antibody and an antigen, wherein the antigen is an active wild type; unattenuated; attenuated; partially inactivated; or totally inactivated infectious pathogen that causes the infection or is equivalent to the pathogen causing the existing infection, and wherein the antibody neutralizes infectivity of either the pathogen causing the existing infection, or the equivalent pathogen, or both. In one embodiment the antibody neutralizes the pathogen, yet allows the natural immune response to the pathogen to develop, thus eliciting a vaccine-like persistent immunological response, while neutralizing the pathological effects of the pathogen. In another embodiment, the antibody neutralizes infectivity of the pathogen and enhances the subject's endogenous immunological response to the pathogen. In yet another embodiment, the antibody neutralizes infectivity of the pathogen and allows the natural immune response process to continue at some level.

In yet another aspect, the invention comprises a kit that comprises an antibody and an antigen, wherein the antigen is an active wild type; unattenuated; attenuated; partially inactivated; or totally inactivated infectious pathogen; and wherein the antibody neutralizes infectivity of the pathogen.

The invention further comprises a pharmaceutical composition comprising an antibody, an antigen, and a pharmaceutically acceptable carrier, diluent, or excipient, wherein the antigen is an active wild type; unattenuated; attenuated; partially inactivated; or totally inactivated infectious pathogen, and wherein the antibody neutralizes infectivity of the pathogen.

DETAILED DESCRIPTION

The invention is derived in part from the discovery of potent antibodies which neutralize most, if not all, genetic variants of viruses (Corti D., et al., 2011, A neutralizing antibody selected from plasma cells that binds to group 1 and group 2 influenza A hemagglutinins. *Science*, 333:850-856) and the discovery of a method of generating a passive and an active immune response in a subject comprising administering a neutralizing antibody and a pathogen to the subject. The invention is further based on the discovery that the use of neutralizing antibodies does not block the generation of immunological memory and long-lasting protection and could, through a series of mechanisms, alter and improve the quality of the immune response to the given pathogen.

The methods of the invention provide a combination of passive and active immunization. The neutralizing antibody prevents or decreases pathogen-induced symptoms without compromising the generation of immunological memory and long-term protection. Further, there may be additional benefits such as a stronger and qualitatively improved, and possibly different, immune response.

Without being bound to any theory, it is believed that the antibody increases presentation of the antigen to B cells and T cells. It is also believed that the antibody skews T helper cell response, i.e., Th1 vs Th2 T cell responses, which could be particularly advantageous for T cell vaccines such as vaccines against tuberculosis or RSV.

By administering a neutralizing antibody and a pathogen, neutralized by the antibody, to a subject, the subject can get immediate protection from the disease or infection caused by the pathogen via the injection of the antibody, and broad, active immunity (both B-cell and T-cell based immunity) in response to the pathogen. This may enable the development of a simple vaccine process, and, importantly, allows development of vaccines for infections or disorders for which vaccines were, until now, difficult to develop. Such infections or disorders are those for which it is difficult to obtain the key epitopes in a form that provokes a broad immunological response required of a vaccine. Examples of such diseases or disorders include, but are not limited to, those caused by pathogens such as human immunodeficiency virus type 1 (HIV-1), human immunodeficiency virus type 2 (HIV-2), hepatitis C (HCV) etc. With the methods of the present invention, it is now possible to elicit a broad immunological response by the administration of such pathogens as well as very potent antibodies that neutralize the infectivity of the pathogens.

In one aspect of the invention, the invention comprises methods for generating, stimulating or eliciting a passive and an active vaccine or immune response in a subject, or ameliorating or eliminating the severity of an infection in a subject, or limiting infection of a subject by a pathogen.

In one embodiment of the invention, the invention comprises a method of generating an active vaccine or immune response in a subject comprising administering to the subject an effective amount of an antibody and an antigen. The antigen administered is an active wild type; unattenuated; attenuated; partially inactivated; or totally inactivated infectious pathogen that causes a disease or disorder, and the antibody is a neutralizing antibody that neutralizes infectivity of the pathogen.

In another embodiment, the invention comprises a method of ameliorating or eliminating the severity of an infection caused by an active wild type; unattenuated; attenuated; partially inactivated; or totally inactivated infectious pathogen, comprising administering to a subject in need thereof, an effective amount of an antibody and an antigen. The antigen administered is the pathogen that causes the infection or disease or an equivalent thereof, and the antibody is a neutralizing antibody that neutralizes infectivity of the pathogen that causes the disease, the equivalent pathogen or both.

In yet another embodiment, the invention comprises a method of limiting infection of a subject by an active wild type; unattenuated; attenuated; partially inactivated; or totally inactivated infectious pathogen, comprising administering to a subject in need of such protection an effective amount of an antibody and an antigen. The antigen administered is the pathogen that causes the infection, disorder or disease, or an equivalent thereof, and the antibody is a neutralizing antibody that neutralizes infectivity of the pathogen that causes the disease, the equivalent pathogen or both.

In one embodiment, the subject is immunologically protected from the antigenic pathogen by the active immune response, the antibody, or both. The response is, in general, robust, persistent and fully protective. The protection may, but need not be, greater than the protection seen when the subject is naturally infected by the pathogen and subsequently recovers from such infection. In one embodiment, the protection afforded by the methods of the invention is greater than the protection seen when the subject is naturally infected by the pathogen and subsequently recovers from such infection. In another embodiment, the two types of protection are comparable.

The antigen can be any wild type; unattenuated; attenuated; partially inactivated; or totally inactivated; but infectious pathogen, now known to one of skill in the art, or later discovered, that causes an infection, disease or disorder and for which neutralizing or protective antibodies can be obtained. In one embodiment, the antigen is a pathogen now known to one of skill in the art, or later discovered, that causes a disease or disorder for which potent and broadly protective neutralizing antibodies can be obtained.

Examples of pathogens that can be used as antigens of the invention include, but are not limited to, viral, bacterial, protozoan or fungal pathogens. In one embodiment, the pathogen is a mammalian or avian pathogen. In another embodiment, the pathogen is a human pathogen. In yet another embodiment, the pathogen is selected from the list including, but not limited to, human immunodeficiency virus type 1 (HIV-1), human immunodeficiency virus type 2 (HIV-2), simian immunodeficiency virus (SIV), simian-HIV (SHIV), feline immunodeficiency virus (FIV), hepatitis A virus, hepatitis B virus, hepatitis C virus, herpes simplex virus type 1 or type 2, SARS coronavirus, measles virus, mumps virus, rubella virus, rabies virus, ebola virus, influenza A virus, influenza B virus, papillomavirus, rhinovirus, vaccinia virus, varicella-zoster virus, variola virus, polio virus, rhino virus, respiratory syncytial virus (RSV), metapneumovirus (MPV), dengue virus, a human endogenous retrovirus, *P. falciparum, P. vivax, P. malariae, P. ovale, Corynebacterium diphtheriae, Clostridium tetani, Clostridium botulinum, Bordetella pertussis, Haemophilus influenzae, Neisseria meningitidis*, serogroup A, B, C, W135 and/or Y, *Streptococcus pneumoniae, Streptococcus agalactiae, Streptococcus pyogenes, Staplaylococcus aureus, Bacillus anthracis, Moraxella catarrhalis, Chlamydia trachomatis, Chlamydia pneumoniae, Yersinia pestis, Francisella tularensis, Salmonella* species, *Vibrio cholerae*, toxic *E. coli, Mycobaterium tuberculosis, Burkholderia pseudomallei* and other microbial pathogens.

The invention also comprises a method of ameliorating or eliminating the severity of an existing infection caused by an active wild type; unattenuated; attenuated; partially inactivated; or totally inactivated infectious pathogen, comprising administering to a subject in need thereof, an effective amount of an antibody and an antigen. The antigen is a pathogen that causes the existing infection, or is equivalent to the pathogen causing the existing infection, and the antibody is a neutralizing antibody that neutralizes infectivity of either the pathogen causing the existing infection, or the equivalent pathogen, or both.

In the case of an existing infection, the antigen administered can, but need not be, an infectious pathogen. In one embodiment, the antigen is an active wild type; live, unattenuated; attenuated; partially inactivated; or totally inactivated, but infectious pathogen as described above, that is equivalent to the pathogen causing the existing infection. In another embodiment, the antigen is an attenuated or partially or totally inactivated, or non-infectious pathogen that is equivalent to the pathogen causing the existing infection.

In yet another embodiment of the invention, the invention provides a method of ameliorating or eliminating the severity of an existing infection caused by an active wild type; unattenuated; attenuated; partially inactivated; or totally inactivated infectious pathogen, comprising administering to a subject in need thereof an effective amount of an antibody. The antibody administered enhances the subject's endogenous or active immunological response to the pathogen and neutralizes infectivity of the pathogen. This is seen, for example, in individuals infected with highly pathogenic viruses such as H5N1 virus and SARS virus.

In another aspect, the invention provides a kit that comprises an antibody and/or an antigen. In one embodiment, the antigen is an infectious pathogen as described above and the antibody neutralizes infectivity of the pathogen. In another embodiment, the antigen is an attenuated or partially or completely inactivated, or non-infectious pathogen as described above. In yet another embodiment, the antibody enhances the subject's endogenous or active immunological response to the pathogen and neutralizes infectivity of the pathogen.

In yet another aspect, the invention provides a pharmaceutical composition comprising an antibody and/or an antigen, and a pharmaceutically acceptable carrier, diluent, or excipient. In one embodiment, the antigen is an infectious pathogen as described above and the antibody neutralizes infectivity of the pathogen. In another embodiment, the antigen is an attenuated or partially or totally inactivated, or non-infectious pathogen as described above. In yet another embodiment, the antibody enhances the subject's endogenous or active immunological response to the pathogen and neutralizes infectivity of the pathogen.

In the methods of the invention the antibody and antigen may be administered concurrently or sequentially. In one embodiment, the antibody and antigen are administered concurrently, i.e., they are administered simultaneously, or within a few seconds, for example, within one (1) or two (2) seconds, of each other.

In other embodiments, the antibody and antigen may be administered sequentially. In one embodiment, the antibody is administered first, followed by administration of the antigen. In another embodiment, the antigen is administered first, followed by administration of the antibody. In yet another embodiment, the antibody and the antigen are administered concurrently. In still another embodiment, the antibody and the antigen are administered as an antibody-antigen complex.

In those embodiments of the invention where the antibody and antigen are administered sequentially, i.e., antibody first, followed by antigen, or antigen first, followed by antibody, the time interval between the administration of the first and second moieties could be as little as a few seconds, for example, two, three, four, five, or ten seconds, or could be as large as one day or several days, for example, two, three, four, five, six, eight, ten or twelve days, or even weeks, for example, one, two, three or four weeks. In one embodiment, the time interval ranges from about 5 seconds to about 3 weeks.

In another embodiment, the time interval ranges from about 5 seconds to about 2 weeks, or from about 5 seconds to about 10 days, or from about 5 seconds to about 1 week, or from about 5 seconds to about 5 days, or from about 5 seconds to about 4 days, or from about 5 seconds to about 3 days, or from about 5 seconds to about 2 days, or from about 5 seconds to about 36 hours, or from about 5 seconds to about 1 day, or from about 5 seconds to about 18 hours, or from about 5 seconds to about 12 hours, or from about 5 seconds to about 8 hours, or from about 5 seconds to about 6 hours, or from about 5 seconds to about 4 hours, or from about 5 seconds to about 2 hours, or from about 5 seconds to about 1 hour, or from about 5 seconds to about 45 minutes, or from about 5 seconds to about 30 minutes, or from about 5 seconds to about 20 minutes, or from about 5 seconds to about 15 minutes, or from about 5 seconds to about 10 minutes, or from about 5 seconds to about 5 minutes, or from about 5 seconds to about 3 minutes, or from about 5 seconds to about 1 minute, or from about 5 seconds to about 30 seconds.

In yet another embodiment, the time interval ranges from about 10 seconds to about 3 weeks, or from about 15 seconds to about 3 weeks, or from about 30 seconds to about 3 weeks, or from about 45 seconds to about 3 weeks, or from about 1 minute to about 3 weeks, or from about 2 minutes to about 3 weeks, or from about 3 minutes to about 3 weeks, or from about 5 minutes to about 3 weeks, or from about 7 minutes to about 3 weeks, or from about 10 minutes to about 3 weeks, or from about 15 minutes to about 3 weeks, or from about 20 minutes to about 3 weeks, or from about 30 minutes to about 3 weeks, or from about 45 minutes to about 3 weeks, or from about 1 hour to about 3 weeks, or from about 2 hours to about 3 weeks, or from about 3 hours to about 3 weeks, or from about 4 hours to about 3 weeks, or from about 6 hours to about 3 weeks, or from about 8 hours to about 3 weeks, or from about 12 hours to about 3 weeks, or from about 18 hours to about 3 weeks, or from about 1 day to about 3 weeks, or from about 36 hours to about 3 weeks, or from about 2 days to about 3 weeks, or from about 3 days to about 3 weeks, or from about 4 days to about 3 weeks, or from about 7 days to about 3 weeks, or from about 1 week to about 3 weeks, or from about 2 weeks to about 3 weeks.

In yet another embodiment, the time interval ranges from about 10 seconds to about 2 weeks, or from about 15 seconds to about 10 days, or from about 30 seconds to about 10 days, or from about 1 minute to about 10 days, or from about 2 minutes to about 10 days, or from about 5 minutes to about 10 days, or from about 10 minutes to about 10 days, or from about 20 minutes to about 10 days, or from about 30 minutes to about 10 days, or from about 1 hour to about 10 days, or from about 2 hours to about 10 days, or from about 4 hours to about 10 days, or from about 6 hours to about 10 days, or from about 8 hours to about 10 days, or from about 12 hours to about 10 days, or from about 18 hours to about 10 days, or from about 24 hours to about 10 days, or from about 36 hours to about 10 days, or from about 2 days to about 10 days, or from about 3 days to about 10 days, or from about 4 days to about 10 days, or from about 5 days to about 10 days, or from about 7 days to about 10 days.

The time interval between the administration of the antibody and the antigen, or the antigen and the antibody, could be important in optimizing the effect. This time interval will depend on several factors, such as the dosage of the antibody and the antigen, the degree of infectivity of the antigenic pathogen, the route of administration of the antibody and the antigen, the immune system of the subject etc. One of skill in the art would have the knowledge to adjust the time interval based on these factors in order to ascertain the optimum effect.

In addition to the time interval, the dose or quantity or concentration of the antibody and antigen is also important. As described in Example 1 below, the doses of the antibody and/or the antigen need to be controlled such that the subject is protected against infection by the pathogen, while allowing the body to generate the endogenous immune response. The antibody should not completely interfere with replication of the pathogen. The right balance will reduce the infectivity (and symptoms) without completely abolishing the generation of antigenic material necessary to elicit the immune response. The dose should be established case by case, but the principle to be followed is that the antibody dose and administration schedule should be tuned to not confer full neutralization or blocking of the pathogen replication.

The dose of antibody administered will depend on several factors including, but not limited to, the potency of the antibody, the route of administration as discussed below, the immune system of the subject, whether the antibody is being administered before, or after, the antigen, etc. One of skill in the art would have the knowledge to adjust the dose of the antibody based on these factors. In one embodiment, the antibody is administered at doses from about 0.01 mg/kg (10 ng/kg) to about 100 mg/kg. In another embodiment, the antibody is administered at doses from about 0.01 mg/kg to about 75 mg/kg, or from about 0.01 mg/kg to about 50 mg/kg, or from about 0.05 mg/kg (5 ng/kg) to about 100 mg/kg, or from about 0.05 mg/kg to about 75 mg/kg, or from about 0.01 mg/kg to about 50 mg/kg, or from about 0.1 mg/kg to about 100 mg/kg, or from about 0.1 mg/kg to about 75 mg/kg, or from about 0.1 mg/kg to about 50 mg/kg.

In another embodiment, the antibody is administered at doses from about 0.1 mg/kg to about 45 mg/kg, or from about 0.1 mg/kg to about 40 mg/kg, or from about 0.1 mg/kg to about 35 mg/kg, or from about 0.1 mg/kg to about 30 mg/kg, or from about 0.1 mg/kg to about 25 mg/kg, or from about 0.1 mg/kg to about 20 mg/kg, or from about 0.1 mg/kg to about 15 mg/kg, or from about 0.1 mg/kg to about 10 mg/kg, or from about 0.1 mg/kg to about 5 mg/kg, or from about 0.1 mg/kg to about 4 mg/kg, or from about 0.1 mg/kg to about 3 mg/kg, or from about 0.1 mg/kg to about 2 mg/kg, or from about 0.1 mg/kg to about 1 mg/kg, or from about 0.1 mg/kg to about 0.8 mg/kg, or from about 0.1 mg/kg to about 0.6 mg/kg, or from about 0.1 mg/kg to about 0.5 mg/k, or from about 0.1 mg/kg to about 0.3 mg/kg, or from about 0.01 mg/kg to about 1 mg/kg, or from about 0.01 mg/kg to about 0.0.8 mg/kg, or from about 0.01 mg/kg to about 0.6 mg/kg, or from about 0.01 mg/kg to about 0.5 mg/kg, or from about 0.01 mg/kg to about 0.3 mg/kg, or from about 0.01 mg/kg to about 0.1 mg/kg.

In yet another embodiment, the antibody is administered at doses from about 0.2 mg/kg to about 50 mg/kg, or from about 0.5 mg/kg to about 50 mg/kg, or from about 1 mg/kg to about 50 mg/kg, or from about 2 mg/kg to about 50 mg/kg, or from about 3 mg/kg to about 50 mg/kg, or from about 4 mg/kg to about 50 mg/kg, or from about 5 mg/kg to about 50 mg/kg, or from about 10 mg/kg to about 50 mg/kg, or from about 15 mg/kg to about 50 mg/kg, or from about 20 mg/kg to about 50 mg/kg, or from about 25 mg/kg to about 50 mg/kg, or from about 30 mg/kg to about 50 mg/kg, or from about 35 mg/kg to about 50 mg/kg, or from about 40 mg/kg to about 50 mg/kg, or from about 45 mg/kg to about 50 mg/kg, or from about 30 mg/kg to about 75 mg/kg, or from about 40 mg/kg to about 75 mg/kg, or from about 30 mg/kg to about 100 mg/kg, or from about 40 mg/kg to about 50 mg/kg, or from about 50 mg/kg to about 70 mg/kg, or from about 50 mg/kg to about 80 mg/kg, or from about 50 mg/kg to about 90 mg/kg, or from about 50 mg/kg to about 100 mg/kg, or from about 70 mg/kg to about 90 mg/kg, or from about 70 mg/kg to about 100 mg/kg.

In still another embodiment, the antibody is administered at doses from about 1 mg/kg to about 3 mg/kg, or from about 1 mg/kg to about 5 mg/kg, or from about 1 mg/kg to about 7 mg/kg, or from about 1 mg/kg to about 10 mg/kg, or from about 5 mg/kg to about 10 mg/kg, or from about 5 mg/kg to about 15 mg/kg, or from about 5 mg/kg to about 20 mg/kg, or from about 10 mg/kg to about 15 mg/kg, or from about 10 mg/kg to about 20 mg/kg, or from about 10 mg/kg to about 25 mg/kg, or from about 10 mg/kg to about 30 mg/kg, or from about 15 mg/kg to about 20 mg/kg, or from about 15 mg/kg to about 25 mg/kg, or from about 15 mg/kg to about 30 mg/kg, or from about 15 mg/kg to about 35 mg/kg, or from about 20 mg/kg to about 25 mg/kg, or from about 20 mg/kg to about 30 mg/kg, or from about 20 mg/kg to about 35 mg/kg, or from about 20 mg/kg to about 40 mg/kg, or from about 25 mg/kg to about 30 mg/kg, or from about 25 mg/kg to about 35 mg/kg, or from about 25 mg/kg to about 40 mg/kg, or from about 25 mg/kg to about 45 mg/kg, or from about 25 mg/kg to about 50 mg/kg.

Just as with the antibody, the dose of antigen administered varies from case to case, and will depend on several factors, including, but not limited to, the potency of the antibody that is being administered, the infectivity of the antigen, the route of administration as discussed below, the immune system of the subject, whether the antigen is being administered before, or after, the antibody, etc. One of skill in the art would have the knowledge to adjust the dose of the antigen based on these factors. In one embodiment, the antigen is an active wild type; unattenuated; attenuated; partially inactivated; or totally inactivated, but infectious pathogen and is administered at doses from about 1 infectious or colony forming unit to about $10^{10}$ infectious or colony forming units.

In another embodiment, the antigen is an active wild type; unattenuated; attenuated; partially inactivated; or totally inactivated, but infectious pathogen and is administered at doses from about 1 infectious or colony forming unit to about $10^9$ infectious or colony forming units, or from about 1 infectious or colony forming unit to about $10^8$ infectious or colony forming units, or from about 1 infectious or colony forming unit to about $10^7$ infectious or colony forming units, or from about 1 infectious or colony forming unit to about $10^6$ infectious or colony forming units, or from about 1 infectious or colony forming unit to about $10^5$ infectious or colony forming units, or from about 1 infectious or colony forming unit to about $10^4$ infectious or colony forming units, or from about 1 infectious or colony forming unit to about 5000 infectious or colony forming units, or from about 1 infectious or colony forming unit to about 1000 infectious or colony forming units, or from about 1 infectious or colony forming unit to about 500 infectious or colony forming units, or from about 1 infectious or colony forming unit to about 100 infectious or colony forming units, or from about 1 infectious or colony forming unit to about 50 infectious or colony forming units, or from about 1 infectious or colony forming unit to about 10 infectious or colony forming units, or from about 1 infectious or colony forming unit to about 5 infectious or colony forming units.

In another embodiment, the antigen is an active wild type; unattenuated; attenuated; partially inactivated; or totally inactivated, but infectious pathogen and is administered at doses from about 10 infectious or colony forming units to about $10^{10}$ infectious or colony forming units, or from about 50 infectious or colony forming units to about $10^{10}$ infectious or colony forming units, or from about 100 infectious or colony forming units to about $10^{10}$ infectious or colony forming unit, or from about 500 infectious or colony forming units to about $10^{10}$ infectious or colony forming units, or from about 1000 infectious or colony forming units to about $10^{10}$ infectious or colony forming units, or from about $10^4$ infectious or colony forming units to about $10^{10}$ infectious or colony forming units, or from about $10^5$ infectious or colony forming unit to about $10^{10}$ infectious or colony forming units, or from about $10^6$ infectious or colony forming units to about $10^{10}$ infectious or colony forming units, or from about $10^7$ infectious or colony forming units to about $10^{10}$ infectious or colony forming units, or from about $10^7$ infectious or colony forming units to about $10^{10}$ infectious s or colony forming units, or from about $10^8$ infectious or colony forming units to about $10^{10}$ infectious or colony forming units, or from about $10^9$ infectious or colony forming units to about $10^{10}$ infectious or colony forming units.

In yet another embodiment, the antigen is an active wild type; unattenuated; attenuated; partially inactivated; or totally inactivated, but infectious pathogen and is administered at doses from about 10 infectious or colony forming units to about 50 infectious or colony forming units, or from about 10 infectious or colony forming units to about 100 infectious or colony forming units, or from about 10 infectious or colony forming units to about 500 infectious or colony forming unit, or from about 10 infectious or colony forming units to about 1000 infectious or colony forming units, or from about 50 infectious or colony forming units to about 500 infectious or colony forming units, or from about 50 infectious or colony forming units to about 1000 infectious or colony forming units, or from about 50 infectious or colony forming unit to about 5000 infectious or colony forming units, or from about 100 infectious or colony forming units to about 1000 infectious or colony forming units, or from about 100 infectious or colony forming units to about 5000 infectious or colony forming units, or from about 100 infectious or colony forming units to about $10^4$ infectious or colony forming units, or from about 500 infectious or colony forming units to about 5000 infectious or colony forming units, or from about 500 infectious or colony forming units to about $10^4$ infectious or colony forming units or from about 500 infectious or colony forming units to about $10^5$ infectious or colony forming units, or from about 1000 infectious or colony forming units to about $10^4$ infectious or colony forming units, or from about 1000 infectious or colony forming units to about $10^5$ infectious or colony forming units, or from about $10^4$ infectious or colony forming units to about $10^5$ infectious or colony forming units, or from about $10^4$ infectious or colony forming units to about $10^6$ infectious or colony forming units, or from about $10^5$ infectious or colony forming units to about $10^6$ infectious or colony forming units, or from about $10^5$ infectious or colony forming units to about $10^7$ infectious or colony forming units, or from about $10^6$ infectious or colony forming units to about $10^7$ infectious or colony forming units, or from about $10^6$ infectious or colony forming units to about $10^8$ infectious or colony forming units, or from about $10^7$ infectious or colony forming units to about $10^8$ infectious or colony forming units, or from about $10^7$ infectious or colony forming units to about $10^9$ infectious or colony forming units, or from about $10^8$ infectious or colony forming units to about $10^9$ infectious or colony forming units, or from about $10^8$ infectious or colony forming units to about $10^{10}$ infectious or colony forming units, or from about $10^9$ infectious or colony forming units to about $10^{10}$ infectious or colony forming units.

In another embodiment, the antigen is an attenuated, partially inactivated, or non-infectious pathogen and is administered at doses from about 0.1 µg to about 1000 µg, or from about 0.1 µg to about 750 µg, or from about 0.1 µg to about 500 µg, or from about 0.1 µg to about 250 µg, or from about 0.1 µg to about 100 µg, or from about 0.1 µg to about 50 µg, or from about 0.1 µg to about 25 µg, or from about 0.1 µg to about 10 µg, or from about 0.1 µg to about 5 µg, or from about 0.1 µg to about 1 µg, or from about 1 µg to about 1000 µg, or from about 5 µg to about 1000 µg, or from about 10 µg to about 1000 µg, or from about 25 µg to about 1000 µg, or from about 50 µg to about 1000 µg, or from about 75 µg to about 1000 µg, or from about 100 µg to about 1000 µg, or from about 200 µg to about 1000 µg, or from about 400 µg to about 1000 µg, or from about 500 µg to about 1000 µg, or from about 600 µg to about 1000 µg, or from about 700 µg to about 1000 µg, or from about 800 µg to about 1000 µg, from about 900 µg to about 1000 µg.

The invention further contemplates the administration of multiple doses of antibody and antigen. In one embodiment, 1, 2, 3, or more doses of the antibody are administered. In another embodiment, 1, 2, 3, or more doses of the antigen are administered. The doses of antibody and antigen may be administered concurrently or sequentially, as discussed above. Further, if the doses of antibody and antigen are administered sequentially, they may be administered in any order, and with the time intervals as discussed above.

The route of administration of the antibody and antigen is also important as different routes confer different rates and levels of bioavailability as well as result in the elicitation of different response mechanisms. In the methods, kits and pharmaceutical compositions of the invention the antibody and antigen may be administered by either the same, or by different routes. In one embodiment, the antibody and the antigen are administered by the same route. In another embodiment, the antibody and the antigen are administered by different routes. Examples of such routes include, but are not limited to, oral, dermal, intranasal, intramuscular, intravenous, intrathecal, intravaginal, intravitreal, rectal administration, subcutaneous, intra-arterial, intramedullary, intraperitoneal, intraventricular, transdermal, transcutaneous, topical, enteral or sublingual.

The antibody used in the methods, kits and pharmaceutical compositions of the invention may be monoclonal or polyclonal; they may be human antibodies or humanized antibodies. In addition, they may be antibody fragments that have retained their ability to bind the antigen as well as their protective/neutralizing ability. In one embodiment, the antibodies are very potent and only a low concentration of the antibodies is needed for neutralizing the pathogen. In another embodiment, the antibodies are very broadly neutralizing and have the ability to neutralize several strains, clades, sub-groups or groups of a pathogen.

The antibody may be isolated, and may be provided in purified form. Typically, the antibody will be present in a composition that is substantially free of other polypeptides e.g., where less than 90% (by weight), usually less than 60% and more usually less than 50% of the composition is made up of other polypeptides.

The antibody can be of any isotype (e.g., IgA, IgG, IgM i.e. an α, γ or µ heavy chain). Within the IgG isotype, the antibodies may be IgG1, IgG2, IgG3 or IgG4 subclass. The antibodies may have a κ or a λ light chain.

Production of Antibodies

Antibodies for use in the invention can be made by any method known in the art. For example, the general methodology for making monoclonal antibodies using hybridoma technology is well known (Kohler, G. and Milstein, C., 1975; Kozbar et al. 1983). In one embodiment, the alternative, improved EBV immortalization method described in WO2004/076677 is used.

Using the method described in WO 2004/076677, B cells producing the antibody of the invention can be transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in WO 2010/046775, plasma cells can be cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL gene regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses the use of single-chain Fv fragments (scFv) derived from the heavy and light chains of an antibody of the invention. For example, the invention includes the use of a scFv comprising the CDRs from a neutralizing antibody. Also included are the use of heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. Additional molecules for use in the invention include, but are not limited to, bispecific Fab2, trispecific Fab3, bispecific scFv, and diabodies.

Standard techniques of molecular biology may be used to prepare DNA sequences encoding the antibodies or antibody fragments. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example, *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

Alternatively, antibodies for use in the invention may be produced by (i) expressing a nucleic acid sequence encoding an antibody of interest in a host cell, and (ii) isolating the expressed antibody product. Additionally, the method may include purifying the isolated antibody.

Transformed B cells and cultured plasma cells may be screened for those producing antibodies of the desired specificity or function. The screening step may be carried out by any immunoassay, e.g., ELISA, by staining of tissues or cells (including transfected cells), by neutralization assay or by one of a number of other methods known in the art for identifying desired specificity or function.

Individual transformed B cell clones may be produced from the positive transformed B cell culture. The cloning step for separating individual clones from the mixture of positive cells may be carried out using limiting dilution, micromanipulation, single cell deposition by cell sorting or other methods known in the art.

Nucleic acid from the cultured plasma cells can be isolated, cloned and expressed in HEK293T cells or other known host cells using methods known in the art.

Pharmaceutical Compositions

The invention provides a pharmaceutical composition comprising an antibody and/or an antigen, as described above. The pharmaceutical composition may also contain a pharmaceutically acceptable carrier, diluent or excipient. Although the carrier or excipient may facilitate administration, it should not itself induce the production of antibodies harmful to the individual receiving the composition, nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, like Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavoured). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody can be provided in kit form with sterile water or a sterile buffer.

The compositions of the invention elicit both a cell mediated immune response as well as a humoral immune response.

Medical Treatments and Uses

The antibodies, antigens, and compositions disclosed herein can be used in the present improved methods for generating, stimulating, or eliciting an active vaccine or immune response in a subject, ameliorating or eliminating the severity of an infection in a subject, or limiting infection of a subject by a pathogen, and in the preparation of medicaments for these purposes.

General

As used herein, the term antibody includes a complete antibody as well as antigen binding fragments thereof as described above. The terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

As used herein, an "equivalent" with respect to an infectious pathogen is a pathogen with the same taxonomic description and bearing the relevant antigenic molecules.

The term "comprising" encompasses "including" e.g., a composition "comprising" X may include something additional to X, e.g., X+Y.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder," "infection" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1

The purpose of this experiment is to evaluate whether the administration of a monoclonal neutralizing antibody before infection can influence the endogenous immune response to Influenza A virus infection. This experiment shows the differing levels of protection conferred to mice to which is administered influenza A virus and differing levels of a potent neutralizing antibody, FI6 (see WO 2010/010466).

A neutralizing antibody (FI6) was administered intravenously to mice at different doses (0.1, 1, and 10 mg/kg) 4 hours before intranasal infection with a sub-lethal dose of Influenza A H1N1 A/Puerto Rico/8/34 virus. Body weight loss and survival were followed for 14 days after infection (FIG. 1).

Figure 1:
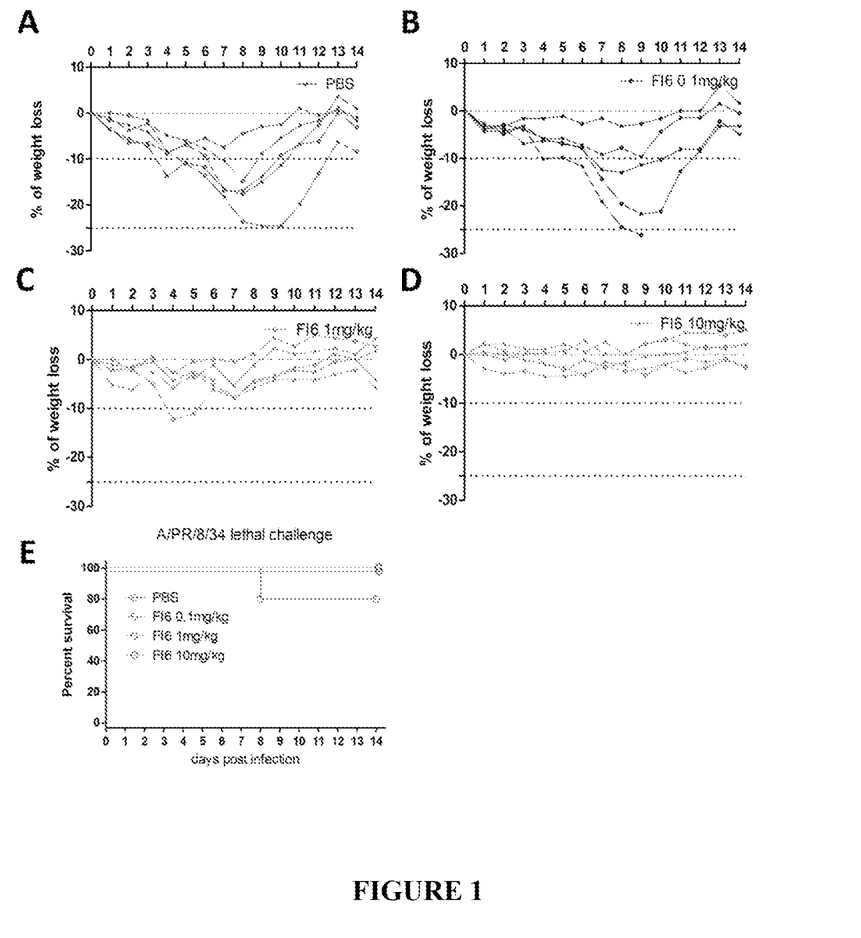
FIG. 1 shows the body weight loss (A to D panels) and survival (E panel) of mice (five animals per group) administered with the indicated doses of the neutralizing antibody FI6 four hours before infection with a sub-lethal challenge with H1N1 A/Puerto Rico/8/34 influenza A virus.

Mice receiving 10 mg/kg FI6 showed no body weight loss and no symptoms (FIG. 1D). Mice receiving 1 mg/kg FI6 showed only a very modest body weight loss without measurable symptoms (ruffled fur and/or respiratory distress) (FIG. 1C), while those receiving 0.1 mg/kg FI6 showed a substantial body weight loss, morbidity, and mortality comparable to the control group of mice receiving phosphate saline buffer only (FIG. 1A-B).

Figure 2:
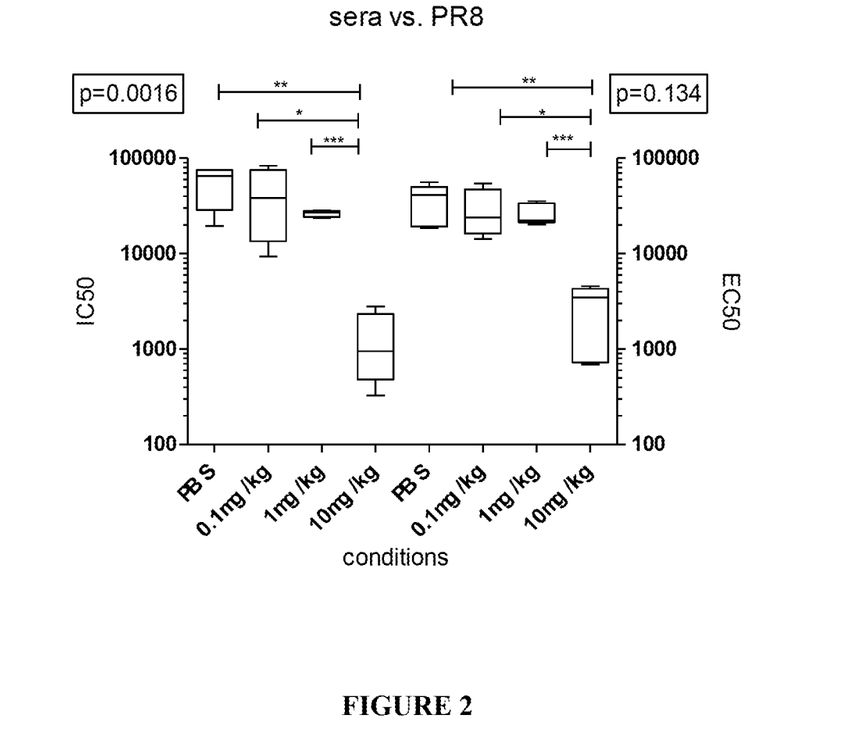
FIG. 2 shows the neutralizing (IC50 left part) and binding (EC50 right part) reciprocal antibody titers in sera of mice collected 25 days after infection and treatment with the indicated doses of FI6.

The immune response in these animals was assessed in serum 25 days after infection by measuring the presence of mouse IgG antibodies able to bind or neutralize the challenge virus (EC50 and IC50 values). Mice treated with 1 mg/kg FI6 showed an immune response significantly greater than that in animals treated with 10 mg/kg antibody, and comparable to the antibody response observed in infected untreated animals (FIG. 2).

These results demonstrate that the administration of a monoclonal neutralizing antibody at an appropriately selected dose is able to contain virus replication and can be instrumental in eliciting, in the absence of severe morbidity, a robust immune response against that specific pathogen.

Example 2

The purpose of this experiment is to evaluate whether the administration of a monoclonal antibody after infection can influence the endogenous immune response to rabies virus infection.

Two rabies virus neutralizing antibodies were administered as a cocktail to Syrian hamsters one or five days after intramuscular infection with a lethal dose of rabies virus. This treatment contained viral spreading into the CNS, decreasing the severity of symptoms and leading to the survival of all treated animals (FIG. 3A).

Figure 3:
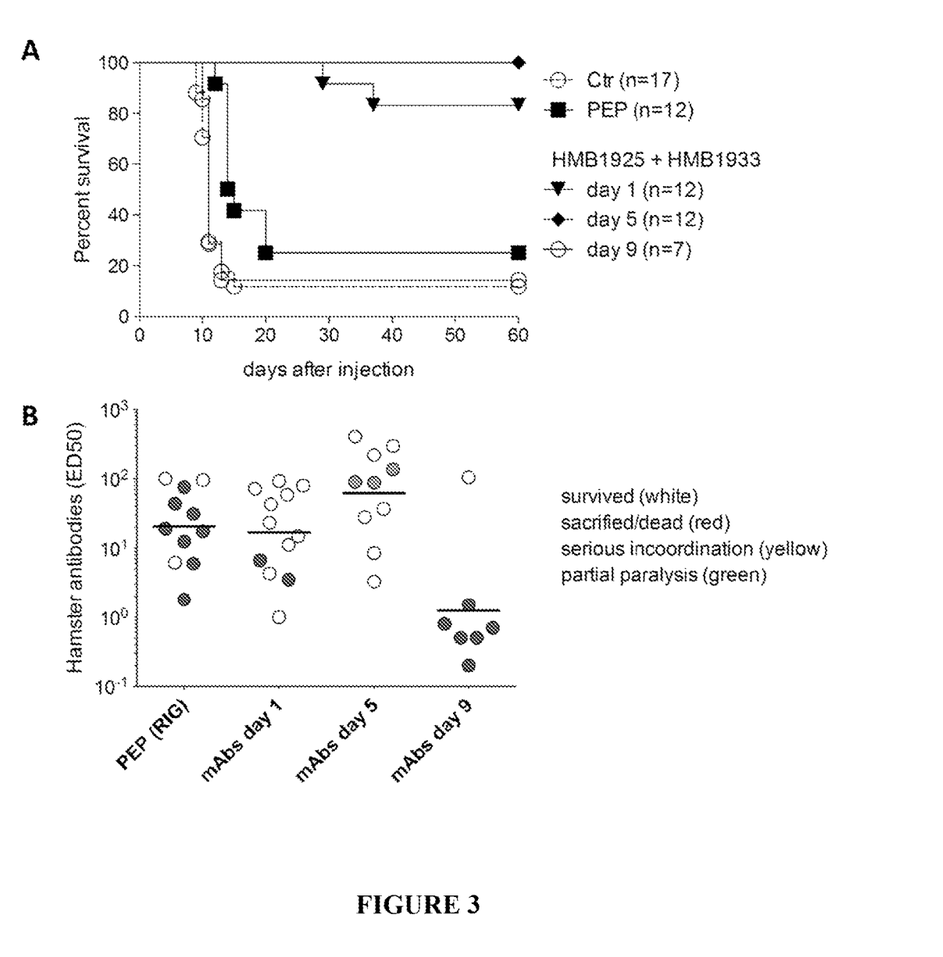
FIG. 3 shows the survival (A) of Syrian hamsters infected with a lethal dose of rabies virus and treated with a combination of two neutralizing antibodies at different time points after infection and the level of production of endogenous anti-rabies antibodies in the different experimental groups (B). PEP, post-exposure prophylaxis given from day one after infection based on rabies vaccine and 20 IU/kg of rabies-specific immunoglobulins (RIG).

Importantly, the antibody treatment did not prevent the production of high levels of endogenous antibodies against the G protein (which is the major target of neutralizing antibodies) (FIG. 3B). The endogenous antibodies, along with T cell responses, might be required to suppress rabies virus spreading and neurologic symptoms.

These results demonstrate that the administration of neutralizing antibodies after infection with a lethal virus not only provide short-term passive protection to the animal but also elicits a robust long-term active endogenous immune response able to further contain virus spreading and related neurologic symptoms.

Each of the references cited herein is incorporated herein by reference in its entirety.

The invention claimed is:

1. A method of generating an active immune response in a subject, comprising administering to said subject an effective amount of an influenza A neutralizing monoclonal antibody sequentially with an influenza A antigen, wherein:
   (a) said influenza A antigen is administered between about 1 hour to about 3 weeks following administration of said monoclonal antibody; or
   (b) said monoclonal antibody is administered between about 1 hour to about 3 weeks following administration of said influenza A antigen; and wherein said influenza A antigen is an attenuated virus or a recombinant vaccine.

2. The method of claim 1, wherein said monoclonal antibody neutralizes infectivity of said influenza A virus.

3. A method of ameliorating or eliminating the severity of an existing influenza A infection or of limiting an existing influenza A infection, comprising generating an active immune response by administering to a subject in need thereof an effective amount of an antibody sequentially with an influenza A antigen, wherein said influenza A antigen is an attenuated virus of said influenza A virus causing said infection, or is a recombinant vaccine derived from said influenza A virus causing said infection;

wherein said antibody neutralizes infectivity of said influenza A virus; and wherein said influenza A antigen is administered between about 1 hour to about 3 weeks following administration of said antibody, or said antibody is administered between about 1 hour to about 3 weeks following administration of said influenza A antigen.

4. The method of claim 1, wherein said subject is immunologically protected from said influenza A antigen.

5. The method of claim 1, wherein said monoclonal antibody and said influenza A antigen are administered by the same route or by different routes.

6. The method of claim 5, wherein said route(s) are selected from the group consisting of oral, dermal, topical, intranasal, intramuscular, intravenous, intrathecal, intravaginal, intravitreal, and subcutaneous.

7. The method of claim 3, wherein said subject is immunologically protected from said influenza A.

8. The method of claim 3, wherein said antibody and said influenza A antigen are administered by the same route or by different routes.

9. The method of claim 8, wherein said route(s) are selected from the group consisting of oral, dermal, topical, intranasal, intramuscular, intravenous, intrathecal, intravaginal, intravitreal, and subcutaneous.

10. The method of claim 3, wherein said antibody enhances said subject's endogenous immunological response to said influenza A virus and neutralizes infectivity of said influenza A virus.

11. The method of claim 3, wherein said antibody is a monoclonal antibody.

12. The method of claim 3, wherein said antibody is FI6.

13. The method of claim 1, wherein said antibody is FI6.

* * * * *